(12) United States Patent
Keller et al.

(10) Patent No.: US 10,518,415 B2
(45) Date of Patent: Dec. 31, 2019

(54) METHOD FOR SAFE COUPLING AND DECOUPLING OF AN INPUT DEVICE

(71) Applicant: KUKA Deutschland GmbH, Augsburg (DE)

(72) Inventors: Henrik Keller, Augsburg (DE); Markus Finke, Königsbrunn (DE); Anja Werling, Munich (DE); Maximilian Heinig, Munich (DE); Horacio Martinez, Munich (DE); Christian Meissner, Augsburg (DE); Mario Miller, Friedberg (DE); Holger Moennich, Friedberg (DE); Thomas Neff, Augsburg (DE); Tobias Reichl, Munich (DE); Nina Sauthoff, Einbeck (DE); Osama Shahin, Augsburg (DE); Oliver Thilmann, Augsburg (DE); Olaf Wegener, Dortmund (DE)

(73) Assignee: KUKA Deutschland GmbH, Augsberg (DE)

( * ) Notice: Subject to any disclaimer, the term of this patent is extended or adjusted under 35 U.S.C. 154(b) by 182 days.

(21) Appl. No.: 15/535,874

(22) PCT Filed: Dec. 3, 2015

(86) PCT No.: PCT/EP2015/078503
§ 371 (c)(1),
(2) Date: Jun. 14, 2017

(87) PCT Pub. No.: WO2016/096456
PCT Pub. Date: Jun. 23, 2016

(65) Prior Publication Data
US 2017/0341233 A1 Nov. 30, 2017

(30) Foreign Application Priority Data
Dec. 17, 2014 (DE) .......................... 10 2014 226 239

(51) Int. Cl.
*B25J 9/16* (2006.01)
*A61B 34/30* (2016.01)
(Continued)

(52) U.S. Cl.
CPC ............. *B25J 9/1676* (2013.01); *A61B 34/30* (2016.02); *A61B 34/70* (2016.02); *B25J 9/1666* (2013.01); *B25J 9/1689* (2013.01); *G05B 19/409* (2013.01)

(58) Field of Classification Search
CPC ...... B25J 9/1676; B25J 9/1666; B25J 9/1689; A61B 34/70; A61B 34/30; G05B 19/409;
(Continued)

(56) References Cited

U.S. PATENT DOCUMENTS

| 8,160,743 B2 * | 4/2012 | Birkenbach | A61B 34/70 318/362 |
| 8,219,245 B2 * | 7/2012 | Merk | B25J 9/102 318/568.24 |

(Continued)

FOREIGN PATENT DOCUMENTS

| CN | 101180591 A | 5/2008 |
| CN | 102011932 A | 4/2011 |

(Continued)

OTHER PUBLICATIONS

German Patent Office; Office Action in German Patent Application No. 10 2014 226 239.9 dated Sep. 16, 2015; 6 pages.
(Continued)

*Primary Examiner* — Jaime Figueroa
(74) *Attorney, Agent, or Firm* — Dorton & Willis, LLP

(57) ABSTRACT

A packaging technique for applying an insulating pack to the housing of a battery cell. The insulating pack is formed from a self-adhesive cutout of insulating material by folding the cutout onto the sides of the housing that are to be covered.
(Continued)

The packaging technique involves a packaging method for automatically applying an insulating pack, a battery cell including an insulating pack, a packaging station for carrying out the method, and a preparation device for preparing one or more cutouts of insulating material.

17 Claims, 3 Drawing Sheets

(51) Int. Cl.
*A61B 34/00* (2016.01)
*G05B 19/409* (2006.01)

(58) Field of Classification Search
CPC ........... G05B 2219/39082; G05B 2219/45171; G05B 2219/45117
USPC .................................................. 700/245, 247
See application file for complete search history.

(56) References Cited

U.S. PATENT DOCUMENTS

| | | | |
|---|---|---|---|
| 8,914,150 B2* | 12/2014 | Moll | A61B 34/30 700/246 |
| 2004/0236874 A1* | 11/2004 | Largman | G06F 21/53 710/8 |
| 2007/0046677 A1 | 3/2007 | Hong et al. | |
| 2007/0129846 A1* | 6/2007 | Birkenbach | A61B 34/70 700/245 |
| 2007/0265731 A1* | 11/2007 | Merk | B25J 9/102 700/245 |
| 2010/0198402 A1 | 8/2010 | Greer et al. | |
| 2011/0060462 A1 | 3/2011 | Aurnhammer et al. | |
| 2012/0185199 A1* | 7/2012 | Moran | G01R 19/2516 702/107 |
| 2012/0239190 A1* | 9/2012 | Finkemeyer | B25J 9/1628 700/245 |
| 2012/0245595 A1 | 9/2012 | Kesavadas et al. | |
| 2013/0231682 A1* | 9/2013 | Barwinkel | A61B 1/00135 606/130 |
| 2014/0135792 A1* | 5/2014 | Larkin | B25J 9/1671 606/130 |
| 2014/0195048 A1* | 7/2014 | Moll | A61B 34/30 700/247 |
| 2014/0303643 A1 | 10/2014 | Ha et al. | |
| 2016/0059412 A1* | 3/2016 | Oleynik | B25J 9/163 700/257 |
| 2016/0135816 A1* | 5/2016 | Lavallee | A61B 17/15 606/88 |
| 2016/0136814 A1* | 5/2016 | Garde | B25J 9/1674 700/264 |

FOREIGN PATENT DOCUMENTS

| | | |
|---|---|---|
| CN | 102350700 A | 2/2012 |
| CN | 103492133 A | 1/2014 |
| DE | 102012206350 A1 | 10/2013 |
| EP | 1876505 A1 | 1/2008 |
| EP | 2113344 A1 | 11/2009 |
| EP | 2123407 A2 | 11/2009 |
| JP | 2011206886 A | 10/2011 |
| WO | 2012143044 A1 | 10/2012 |

OTHER PUBLICATIONS

European Patent Office; Search Report and Written Opinion in International Patent Application No. PCT/EP2015/078503 dated Mar. 2, 2016; 15 pages.
Chinese Patent Office; Office Action in related Chinese Patent Application No. 201580069052.7 dated Mar. 4, 2019; 6 pages.
Chinese Patent Office; Search Report in related Chinese Patent Application No. 201580069052.7 dated Feb. 22, 2019; 2 pages.
Chinese Patent Office; Second Office Action in related Chinese Patent Application No. 201580069052.7 dated Sep. 18, 2019; 9 pages.
Chinese Patent Office; Second Search Report in related Chinese Patent Application No. 201580069052.7 dated Sep. 10, 2019; 2 pages.

* cited by examiner

METHOD FOR SAFE COUPLING AND DECOUPLING OF AN INPUT DEVICE

CROSS-REFERENCE

This application is a national phase application under 35 U.S.C. § 371 of International Patent Application No. PCT/EP2015/078503, filed Dec. 3, 2015 (pending), which claims the benefit of German Patent Application No. DE 10 2014 226 239.9.0 filed Dec. 17, 2014, the disclosures of which are incorporated by reference herein in their entirety.

TECHNICAL FIELD

The invention relates to a method for safely coupling and decoupling an input device to and from a manipulator, wherein the input device is designed to control the manipulator and can control the manipulator in the coupled state. The method and the so-controlled manipulator can be used, for example, for a minimally invasive laparoscopic procedure.

BACKGROUND

For many applications in the field of robotics, in particular in the field of telemanipulation, there is a need for input devices that can be moved translationally or rotationally. In the case of telemanipulation the movements of the input device are detected and converted into translational and/or rotational movements of one or more manipulators.

A manipulator is, according to DIN EN ISO 8373, an automatically controlled, freely programmable multi-purpose manipulator, which is programmable in three or more axes, and can be arranged in either a fixed location or in a moveable manner for use, for example, in automatic control technology. A manipulator has grippers, tools or workpieces. Manipulators are also used in the field of medicine, for example, in minimally invasive surgery. In the latter case the manipulator can have a laparoscopic instrument and can process very small structures or enable minimally invasive imaging by holding and guiding an endoscope.

Depending on the application, it may no longer be necessary at certain times or in response to events, such as, for example, due to a signal of a deadman switch or leaving the working space of the manipulator, to convert a user input directly into a manipulator movement. Such an interruption of the conversion of the user inputs into manipulator movements is hereinafter referred to as "decoupling". As a result, after decoupling it may be necessary to allow at a specified time or in response to a specific event the user inputs to be converted again into manipulator movements. This is referred to hereinafter as "coupling".

If the input device or an arm of the manipulator is moved during the decoupled state, then the position and orientation (pose) of the input device and the corresponding, commanded position and orientation (pose) of the manipulator are no longer synchronized. In this case re-coupling would result in an uncontrolled movement of the manipulator into the position and orientation (pose), currently commanded by the input device. Such an uncontrolled movement of a manipulator is undesirable or inadmissible for a safe operation.

The position is determined by means of information with respect to all three translational degrees of freedom and, thus, the location of a point in space. The orientation is determined by means of information with respect to all three degrees of rotational freedom. The combination of position and orientation of an object is referred to as the pose. In order to determine the pose of a point, the point is assigned three spatial axes. In this way all of the six possible degrees of freedom of the point can be determined.

The published document EP 1 876 505 A1 discloses input devices that are equipped with motors or brakes with active axes in order to prevent the input device from moving into the decoupled state. This arrangement makes it possible to hold the input device in the current pose even after decoupling. However, such input devices with active axes are expensive, technically complex and error-prone.

Therefore, the object of the present invention is to enable with simpler means a safe coupling and decoupling of the input device to and from the manipulator. Moreover, the user should be able to operate the system intuitively, and the system should enable a coupling that is as fast and safe as possible.

SUMMARY

The aforementioned engineering objects are achieved by means of a method of the invention for coupling an input device to at least one manipulator, by means of a method for coupling and decoupling an input device to and from at least one manipulator, as well as by means of a corresponding control device, and a machine-readable medium as disclosed herein.

In particular, the aforementioned objects are achieved by means of a method for coupling an input device to a manipulator, wherein the input device is designed to control the manipulator, and the method comprises the following process steps:

a) checking whether the pose of an input point of the input device is within an input tolerance range, wherein the input tolerance range of the input device is determined by mapping a tolerance range of a reference point of the manipulator; and the input tolerance range is unchangeable up to the coupling of the input device to the manipulator;

b) moving the reference point of the manipulator to the pose, commanded by the input device, when the pose of the input point is within the input tolerance range;

c) coupling the input device to the manipulator after the reference point has reached the commanded pose.

The inventive method for coupling an input device to at least one manipulator enables a fast and yet safe coupling, since it is not necessary for the user to bring the manually guided pose of the input point of the input device into conformity with the current pose of the reference point of the manipulator. Instead, the method allows the manipulator to execute a certain limited movement to the pose currently commanded by the input device. Therefore, the manipulator comes "to meet" the input device for a simple and fast coupling, as soon as the input device is moved into an input tolerance range. In this case the movement of the manipulator to the pose of the input device is limited to a safe movement by means of the input tolerance range and also the respective tolerance range of a reference point of the manipulator, so that especially in laparoscopic operations or similar applications no damage will occur. Thus, a coupling of the input device to the manipulator can be carried out quickly, intuitively and yet safely.

Usually each manipulator is assigned an input device, which can be moved in translational and rotational axes. A user manually guides an input point of the input device; and, in so doing, the individual values of the axes of the input device are to be measured and therefrom the pose of the input point in a space is calculated.

Changes in the position of the input point are usually converted directly into corresponding movements of the manipulator. At the same time the pose of the input point corresponds to the pose of a reference point of the manipulator, which is established relative to the manipulator. Preferably the reference point of the manipulator is the tool center point (TCP). If the manipulator reaches an obstacle space or the limit of its working space, then its movement is stopped; and the input device is decoupled from the manipulator.

In order to re-couple, a tolerance range is determined computationally about the reference point of the manipulator. This tolerance range may assume any shape and size for translational movements. The shape and size of the tolerance range are selected, in particular, in such a way that a translational movement of the reference point within the tolerance range is accepted as safe. The size of the tolerance range is dimensioned in an analogous manner. With regard to rotational movements of the reference point about its three possible spatial axes, the tolerance range can also be limited to certain allowable angular deviations, which the reference point of the manipulator may rotate for coupling. Then the manipulator will move to the commanded pose, only if, on the one hand, the position of the input point is within the spatial limits of the input tolerance range; and, on the other hand, the orientation of the input point is within the allowable angular deviations, specified by the tolerance range.

Furthermore, the tolerance range in automatic control technology may be limited, for example, by the machines and workpieces in the surrounding area. In an application in minimally invasive surgery, the tolerance range may also be limited, for example, by risk structures, such as blood vessels, nerves, etc. that are in the surrounding area of the reference point.

The tolerance range of the reference point of the manipulator is mapped to the input range of the input point of the input device and, as a result, determines the input tolerance range. Hence, the positions of the input point in the input tolerance range and the allowable angular deviations (allowable orientation of the input point) correspond with respect to the manipulator to the positions and allowable angular deviations (orientations) of the reference point in the tolerance range.

Preferably the method comprises the following additional process steps of:

d) checking whether the pose of the input point is within an extended input tolerance range and outside the input tolerance range, wherein the extended input tolerance range is greater than the input tolerance range and wherein the extended input tolerance range includes the input tolerance range;

e) determining an approach pose of the reference point, wherein the approach pose is within the tolerance range of the reference point, and the approach pose has a minimum deviation from the pose of the reference point that is commanded by the input device;

f) moving the reference point of the manipulator to the approach pose, when the input point is within the extended input tolerance range and outside the input tolerance range; and g) coupling the input device to the manipulator, after the reference point has reached the approach pose.

Since the reference point of the manipulator does not leave the tolerance range during the movement to the approach pose, this movement is safe.

The extended input tolerance range allows a simplified coupling, because the extended input tolerance range is greater than the input tolerance range, and is, therefore, found more easily by the user. This extended input tolerance range has any shape and size for translational movements, but is larger than the spatial extent of the input tolerance range and includes the input tolerance range in its entirety. The extended input tolerance range with respect to rotational movements comprises the allowable angular deviations of the input tolerance range in its entirety and defines the extended angular deviations that allow a larger angular deviation than the angular variations of the input tolerance range.

The coupling is safe even with the extended input tolerance range, since the reference point of the manipulator moves toward the commanded pose only within its customary tolerance range. Then the coupling has already taken place, when the reference point of the manipulator has reached the approach pose. As a result, it is not necessary for the reference point of the manipulator to reach the exact pose commanded by the input device. In this case the mapping of the input point of the input device to the reference point of the manipulator changes. The change in the mapping can affect all of the axes of the input device and may be both translational and rotational or any combination thereof. The resulting offset between the commanded pose of the input device and the reference point of the manipulator is irrelevant to the user and often also goes unnoticed by the user during user interaction.

In the simplest case the extended input tolerance range corresponds preferably to the input tolerance range scaled by an extension factor. However, the extended input tolerance range and the input tolerance range need not be concentric. Furthermore, the extended angular deviations do not have to be the same for rotational movements in the opposite direction. For example, an extended input tolerance range for rotational movements may allow an extended angular deviation in a clockwise direction by another 5°, for a rotational movement in the counter-clockwise direction, only by 2°. It is also permitted that the input tolerance range and the extended input tolerance range exhibit an at least partially congruent edge or partially congruent angular deviation.

Furthermore, the method comprises preferably a process step, in which prior to the step of moving the reference point of the manipulator, it is checked whether the pose of the reference point of the manipulator violates an obstacle space in the pose or the approach pose, commanded by the input device. An obstacle space is an area that is in the technically possible working space of the manipulator, but may not be approached or traversed by the manipulator. Then any additional checking as to whether an obstacle space is violated increases the safety of the use of the method. Then the manipulator can be, for example, stopped or guided around the obstacle space.

Furthermore, the method comprises preferably a process step, in which the movement of the reference point of the manipulator to the pose, commanded by the input device, in process step b) is terminated, when the input point leaves the input tolerance range before reaching the commanded pose, and the movement of the reference point of the manipulator to the approach pose in the process step f) is terminated, when the input point leaves the extended input tolerance range before reaching the approach pose.

The input point can leave the input tolerance range as well as the extended input tolerance range by means of rotational or translational movements. The termination of the movement of the reference point as a result of leaving the input tolerance range or the extended input tolerance range of the input point prevents the manipulator from following the input device in an uncontrolled manner, without requiring a coupling to have taken place. A movement of the reference point of the manipulator to the coupling pose shall be allowed, only if there is an input point in the input tolerance range or extended input tolerance range.

Preferably the shape and/or size of the tolerance range, the input tolerance range and/or the extended input tolerance range can be a function of at least one other system variable, comprising the speed of the manipulator; a detection range, which enables the detection of the position and/or orientation of the reference point of the manipulator; forces or torques acting on the reference point of the manipulator; an obstacle space determined from the environmental data; and/or a boundary of the working space of the manipulator.

The size of the tolerance range may be adjusted to the environmental conditions and boundary conditions of the manipulator system, in order to allow only safe movements for the coupling.

At higher speeds of the manipulator, the tolerance range can be determined, for example, smaller than at lower speeds.

The position and/or orientation of the reference point of the manipulator can be determined within the detection range. If a manipulator is used in minimally invasive surgery, such as, for example, a laparoscopic operation, the detection range may be, for example, the field of view of the endoscope. In automatic control technology the detection range may be, for example, the field of view of a camera or another sensor system. The adjustment of the shape and size of the tolerance range, the input tolerance range and optionally the extended input tolerance range to the detection range is advantageous, since in the course of coupling the manipulator remains in the detection range; and a new alignment of the sensor system can be dispensed with.

Furthermore, the forces and/or torques acting on the reference point of the manipulator may affect the shape and size of the tolerance range. Therefore, it is preferred that the tolerance range be dynamically adjustable, when a maximum force or maximum torque is exceeded at the reference point. This feature is advantageous when damage is to be expected only after a certain amount of force or a certain amount of torque.

If a manipulator is used in minimally invasive surgery, such as, for example, laparoscopic surgery, then it is possible to use environmental data, for example, endoscopic images, X-ray images or other image data to determine the obstacle spaces. These obstacle spaces may also affect the shape and size of the tolerance range.

Furthermore, the method may comprise preferably the following process step of: automatically determining the extended input tolerance range, wherein the extended input tolerance range corresponds to the input tolerance range scaled by an extension factor. As a result, the extended input tolerance range can be calculated very easily from the input tolerance range. In this case it is preferred that an absolute minimum size of the extended input tolerance range be specified in order to facilitate the coupling even for very small tolerance ranges.

Furthermore, the aforementioned engineering objects are achieved by mean of a method for coupling and decoupling an input device to and from a manipulator, wherein the input device is designed to control the at least one manipulator and wherein said method comprises the following process steps of:

a) decoupling the input device from the manipulator when the reference point of the manipulator has reached an obstacle space or a boundary of the working space;

b) updating the mapping of the pose of the input point of the input device to the pose of the reference point of the manipulator, wherein the current pose of the input point corresponds to the last allowable pose of the reference point of the manipulator;

c) checking whether the input device-commanded pose of the reference point of the manipulator in the updated mapping is outside an obstacle space and inside the working space;

d) coupling the input device to the manipulator when the input device-commanded pose of the reference point of the manipulator is outside the obstacle space and inside the working space.

The decoupling of the input device from the at least one manipulator ensures that the manipulator cannot be moved by the user into an obstacle space, but rather stops at the border to the obstacle space. Reaching the obstacle space and reaching a boundary of the working space are evaluated preferably for rotational and/or translational movements. This feature can also ensure, for example, that in laparoscopic operations the tool or the endoscope always penetrates the skin or abdominal wall of the patient at the same spot.

Both the constant updating of the mapping of the pose of the input point of the input device to the latest allowable pose of the reference point of the manipulator and the subsequent checking as to whether the input device-commanded pose of the reference point of the manipulator is now again outside the obstacle space and inside the working space allow the input device to be coupled to the manipulator, when the input device is moved in a direction that faces away from the obstacle space. As a result, it is possible to decouple from any position of the input device, as long as the movement of the input device goes in a valid direction, i.e., in a direction that faces away from the obstacle space inside the working space.

Another advantage of the method is that the boundary of the obstacle space of the manipulator automatically corresponds to the boundary of the movement space of the input device, if after decoupling up to a mechanical stop, the user continues to move the input device in an invalid direction or rotation. In this way the movement space of the input device can be fully utilized for telemanipulation of the manipulator.

Preferably the checking as to whether the input device-commanded pose of the reference point of the manipulator is outside an obstacle space and inside the working space is carried out in discrete time steps. This feature results in a continuous querying of the position of the input device.

Preferably the checking as to whether the input device-commanded pose of the reference point of the manipulator is outside an obstacle space and inside the working space is a function of a minimum change in the input device-commanded pose of the reference point of the manipulator. Such a minimum change is advantageous because in this way an undesired coupling and decoupling due to the smallest movements, which could be caused, for example, by a tremor of the user or by signal noise, is avoided.

Preferably the speed of the manipulator is a function of at least one system variable, comprising:

a) a detection range, which enables the detection of the position and/or orientation of the reference point of the manipulator, b) forces or torques acting on the reference point of the manipulator, c) an obstacle space determined from the environmental data and/or, d) a boundary of the working space of the manipulator.

The speed of the manipulator is preferably a function of at least one system variable, in order to achieve a safe movement of the manipulator, wherein the system variable is a detection range, which allows detection of the position and/or orientation of the reference point of the manipulator. The speed of the manipulator can also be a function of a boundary of the working space of the manipulator. The system variable may be forces or torques acting on the reference point of the manipulator; and/or it may comprise an obstacle space determined from the environmental data. Thus, the speed of the manipulator, in particular determined at its reference point, may be adjusted to its potential movement for coupling, in order to achieve a coupling that is as fast, but safe as possible.

Preferably a change in the pose of the input point of the input device to the change in the reference point of the manipulator has a translation ratio of $i \geq 1$, preferably $i=2$ to 10, more preferably $i=3$ to 5. At these translation ratios, especially in laparoscopic surgery, larger movements of the input device are converted into smaller movements of the manipulator, an aspect that enables finer operating steps.

Preferably the method may also comprise a process step of automatically adjusting the translation ratio. In this case the translation ratio is preferably a function of at least one of the aforementioned system variables.

The translation ratio, which indicates the size of the change in the pose of the input point of the input device to the size of the change in the pose of the reference point of the manipulator can be determined manually by the user and can also be changed. This feature is particularly advantageous when the manipulator in certain situations is supposed to execute very small movements. Furthermore, the ratio can be adjusted automatically. The translation ratio may be adjusted preferably independently for translational and rotational movements. For example, it is advantageous, if translational movements are translated at a translation ratio of $i \geq 1$; rotational movements, in contrast, are translated at a translation of ratio $i=1$. In principle, the adjustment of the translation ratios can be adjusted preferably to the respective application. If the manipulator is to be moved, for example, into an area, which is surrounded by obstacle spaces that allow only a very small range of movement, then the translation ratio can be automatically increased. In this way the user gains better control of the manipulator.

Preferably the input device outputs a haptic, visual or audible feedback, wherein the feedback from the input device indicates that an obstacle space of the reference point has been reached; and/or that the input device has been coupled to or decoupled from the manipulator; and/or indicates the distance of the input point of the input device from the input tolerance range and/or from the extended input tolerance range and/or from a corresponding allowable pose of the reference point of the manipulator.

A haptic feedback can take place, for example, by means of force feedback or vibration of the input device. A visual feedback can be shown to the user, for example, on a screen or in the form of light signals, such as, for example, by means of LEDs. An audible feedback can take place, for example, by means of a change in the pitch, the volume or the frequency of a sound sequence. A combination of an audible, visual and haptic feedback is also preferred.

Preferably the input device-commanded pose of the reference point of the manipulator may be shown to the user graphically; and the actual pose of the reference point of the manipulator may be virtually superimposed. Thus, the data entry person can track his input into the input device graphically, an aspect that leads to an improvement in the ergonomics and a faster coupling.

The aforementioned engineering objects are also achieved by means of a control device for controlling at least one manipulator by means of an input device for carrying out the method described above, wherein the control device is designed to receive inputs of the input device and to control the manipulator.

The aforementioned engineering objects are also achieved by means of a machine-readable medium, which stores instructions, so that when said instructions are executed by a control device, the control device controls, according to the method described above, a manipulator on the basis of the inputs of an input device.

BRIEF DESCRIPTION OF THE DRAWINGS

Preferred embodiments of the invention are explained in detail below with reference to the drawings. In the drawings

DETAILED DESCRIPTION

Figure 1:
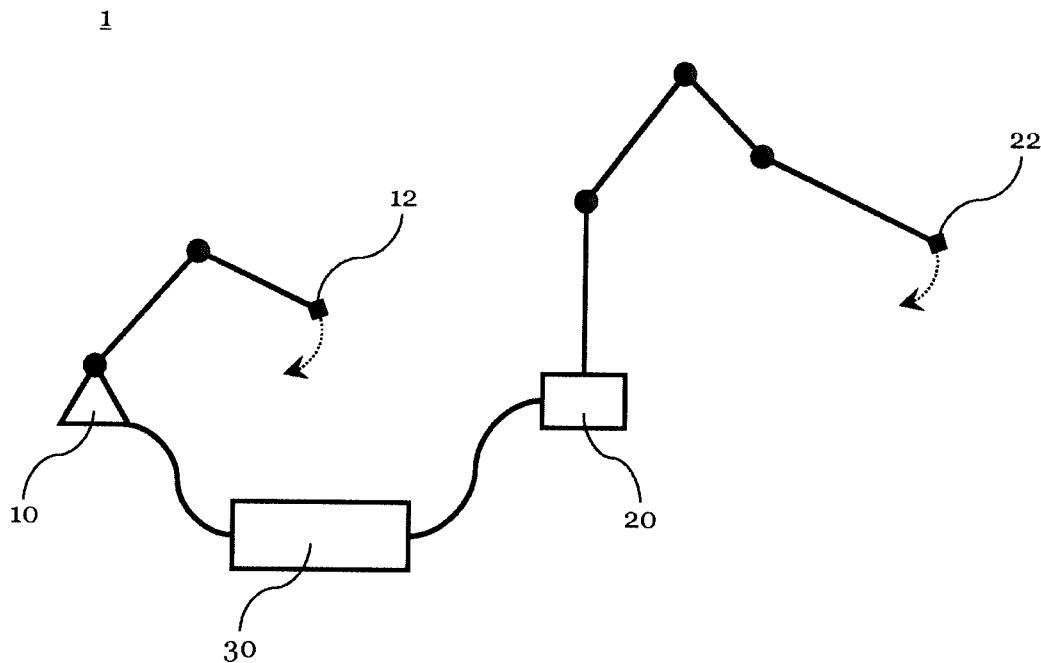
FIG. 1 shows in schematic form a representation of a manipulator system with an input device, a manipulator and a control device.

FIG. 1 shows a manipulator system 1, which comprises an input device 10, a manipulator 20 and a control device 30. A user can move the manipulator 20 by remote control by manually moving the input device 10 (telemanipulation).

The input device 10 can be moved preferably in three translational and three rotational axes. As a result, a user can determine the position and the orientation, i.e., together with the pose, of an input point 12, uniquely defined relative to the input device 10. At least the pose, defined in this way, or a change in the pose of the input point 12 is sent to the control device 30 and received by said control device. The control device 30 converts the change in the pose of the input point 12 into a corresponding change in the pose of a reference point 22 of the manipulator 20. The reference point 22 is fixed relative to the manipulator 20. Preferably the reference point of the manipulator is the hand root point (HWP) of the manipulator or the tool center point (TCP), located at a suitable point of an object guided by the manipulator. The object may be, for example, a medical instrument, a tool, a workpiece or a sensor. For example, the TCP may be defined as a tip of a scalpel, guided by the manipulator.

The number of axes and links of the input device 10 and the manipulator 20 does not have to match, as shown in FIG. 1. If the number of axes and links of the manipulator 20 deviates from the number of axes and links of the input device 10, then a valid position of the manipulator is calculated, in which the pose of the reference point 22 of the manipulator 20 corresponds to the pose commanded by the input device 10. The position of the manipulator is derived from the individual axis values of the axes of the manipulator.

Figure 2:
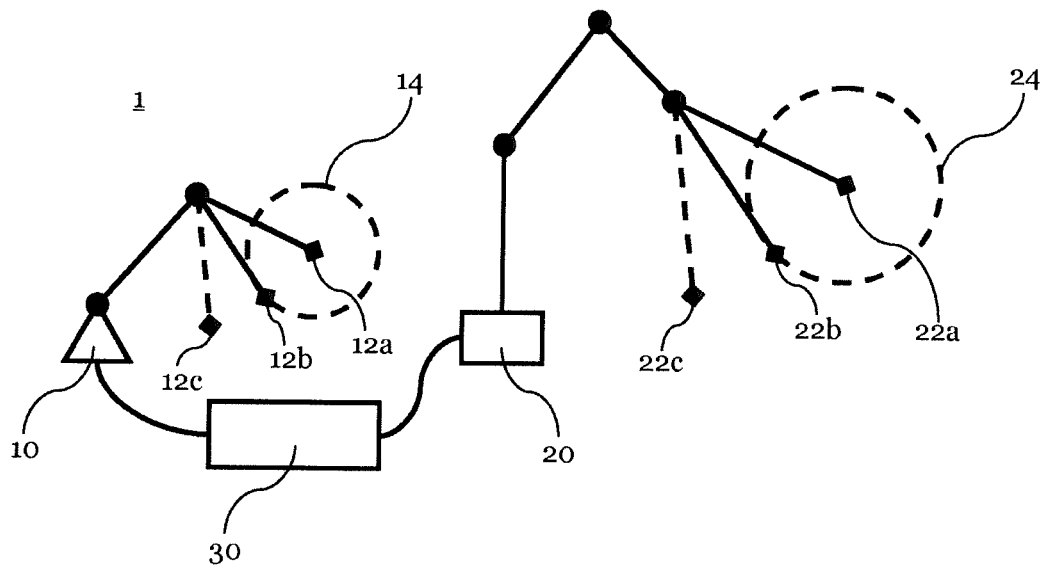
FIG. 2 shows in schematic form a representation of the manipulator system from FIG. 1, with the tolerance range and the input tolerance range, drawn in schematic form.

FIG. 2 shows the manipulator system 1 according to FIG. 1, wherein, for example, three poses (12a, 12b, and 12c) of the input point 12 of the input device 10 are shown. The poses 12a, 12b and 12c of the input point 12 of the input device 10 correspond to the three poses 22a, 22b and 22c of the reference point 22 of the manipulator. A tolerance range 24 is defined around the reference point 22; and for the translational movements of the reference point shown in FIG. 2, this tolerance range corresponds to a sphere having a center point that lies on the reference point 22. The rotational tolerance range, i.e. the allowable angular deviation, is not shown, but is present. The tolerance range 24 is chosen in such a way that a movement of the reference point 22 of the manipulator 20 within the tolerance range 24 can be considered safe. The tolerance range 24 of the reference point of 22 is mapped to the input range of the input point 12 of the input device 10, so that the result is a corresponding input tolerance range 14.

In the pose 12a of the input point 12 and the corresponding pose 22a of the reference point 22, the input device 10 has been decoupled from the manipulator 20. As a result, changes in the pose of the input point 12 of the input device 10 are no longer converted into movements of the manipulator 20. The reference point 22 of the manipulator 20 remains in the pose 22a. If a user moves the input point 12 of the input device 10 in the decoupled state, for example, to the pose 12c of the input point 12, then the pose 22c of the reference point 22 of the manipulator 20 would be commanded. However, the pose 22c of the reference point 22 lies outside the tolerance range 24. In this case coupling is not possible because no safe automatic movement of the reference point 22 of the manipulator 20 from the pose 22a to the pose 22c can be ensured. Consequently, the manipulator 20 does not move; and the reference point 22 remains in the safe pose 22a.

If at this point the user moves the input point 12 of the input device 10, for example, into the pose 12b, which lies within the input tolerance range 14, then the pose 22b is commanded accordingly. This pose 22b is within the tolerance range 24; and, thus, an automatic movement of the manipulator 20 to this pose 22b is considered to be safe. Correspondingly a movement of the reference point 22 of the manipulator 20 to the commanded pose 22b occurs. For safety reasons such a movement takes place at a defined speed. Therefore, the manipulator 20 moves automatically, so that its reference point 22 comes to meet the input point 12 of the input device 10 at the commanded pose 22b. When the reference point 22 finally reaches the pose 22b, the input device 10 is coupled to the manipulator 20. At this point the user can move the manipulator 20 by remote control (telemanipulation) by manually moving the input device 10 until said input device is decoupled again. By coming to meet the manipulator 20 at the commanded pose, the coupling is faster and easier than in the case, where the user has to hit exactly the current pose or position of the reference point 22 of the manipulator 20 with the input device 10.

Figure 3:
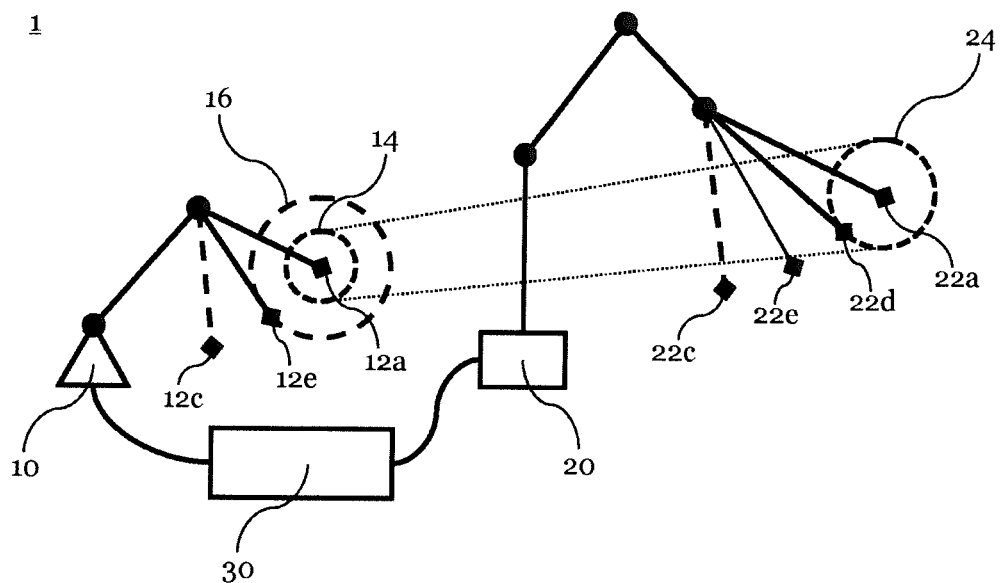
FIG. 3 shows in schematic form a representation of the manipulator system from FIG. 2, with the extended tolerance range, drawn in schematic form.

FIG. 3 shows the manipulator system 1 from FIG. 2, wherein the input tolerance range 14 is supplemented by an extended input tolerance range 16. The extended input tolerance range 16 is preferably concentric to the input tolerance range 14 for translational movements and corresponds preferably to an input tolerance range 14 that is enlarged by an extension factor. The extended input tolerance range for rotational movements, i.e., the extended angular deviations, are not shown, but are present. In the illustrated pose 12a of the input point 12 and the corresponding pose 22a of the reference point 22, the input device 10 has been decoupled from the manipulator 20. During the decoupled state the input point 12 of the input device 10 is moved by the user, for example, into the pose 12c. The pose 12c of the input point 12 corresponds to a commanded pose 22c of the reference point 22. However, the pose 22c of the reference point 22 is outside the tolerance range 24, so that a safe movement of the reference point 22 from the pose 22a to the commanded pose 22c cannot be ensured; and the coupling described above is not possible. In addition, the pose 12c is outside the extended input tolerance range 16. Therefore, the reference point 22 of the manipulator 20 remains in the pose 22a.

If at this point the user moves the input point 12 into the extended input tolerance range 16, for example, here to pose 12e, then the approach pose 22d of the reference point 22 is calculated within the tolerance range 24; where in this case said approach pose exhibits a minimum distance from the commanded pose 22e of the reference point 22. A movement of the reference point 22 to the approach pose 22d can be considered to be safe, since it is within the tolerance range 24. Correspondingly the manipulator 20 is moved in such a way that its reference point 22 is moved to the approach pose 22d.

If the reference point 22 reaches the approach pose 22d, then the input device 10 is coupled to the manipulator 20; and the pose 12e of the input point 12 is assigned the approach pose 22d of the reference point 22. Then the manipulator 20 is controlled by the input device 10 with this new mapping. At this point the mapping has an offset that corresponds to the deviation of the exactly commanded pose 22e of the reference point 22 from the approach pose 22d. The offset can have both a translational and rotational characteristic. In this coupling process the reference point 22 of the manipulator 20 goes to meet the input point 12 of the input device 10 as soon as the input point 12 begins to enter the extended input tolerance range 16 as far as it is allowed by the tolerance range 24 of the reference point 22 and coupling is allowed with the offset mapping. This arrangement makes it possible to perform a safe coupling of the input device 10 to the manipulator 20 in a faster and easier way.

Figure 4A:
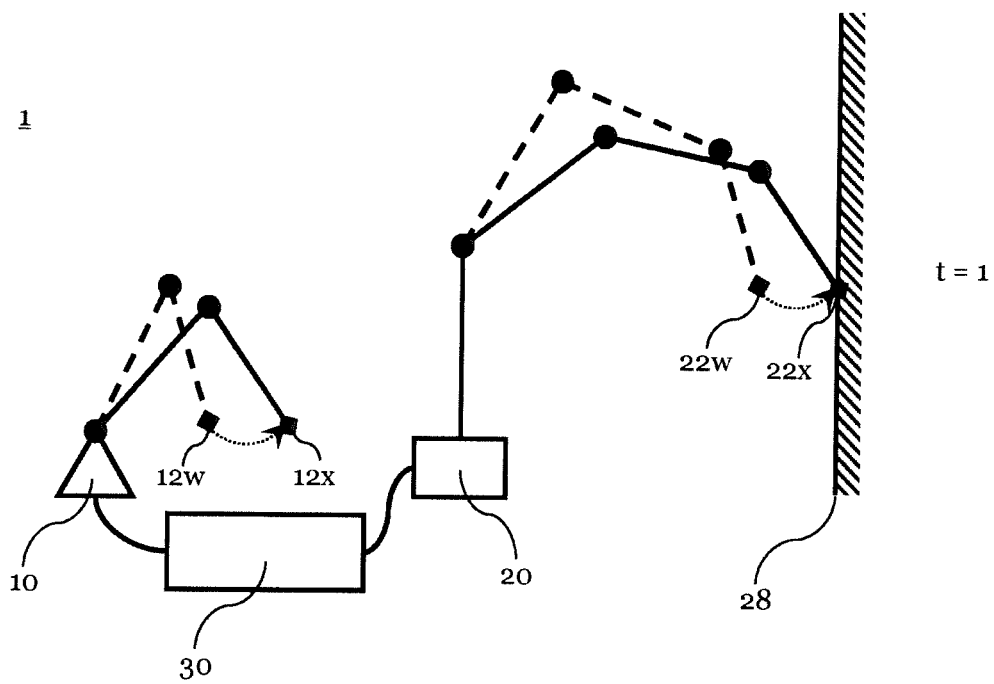
FIGS. 4*a* to 4*c* show in schematic form representations of the manipulator system from FIG. 1, at different times, with an obstacle space, drawn in schematic form, as well as different poses of the input point of the input device and the reference point of the manipulator.
Figure 4B:
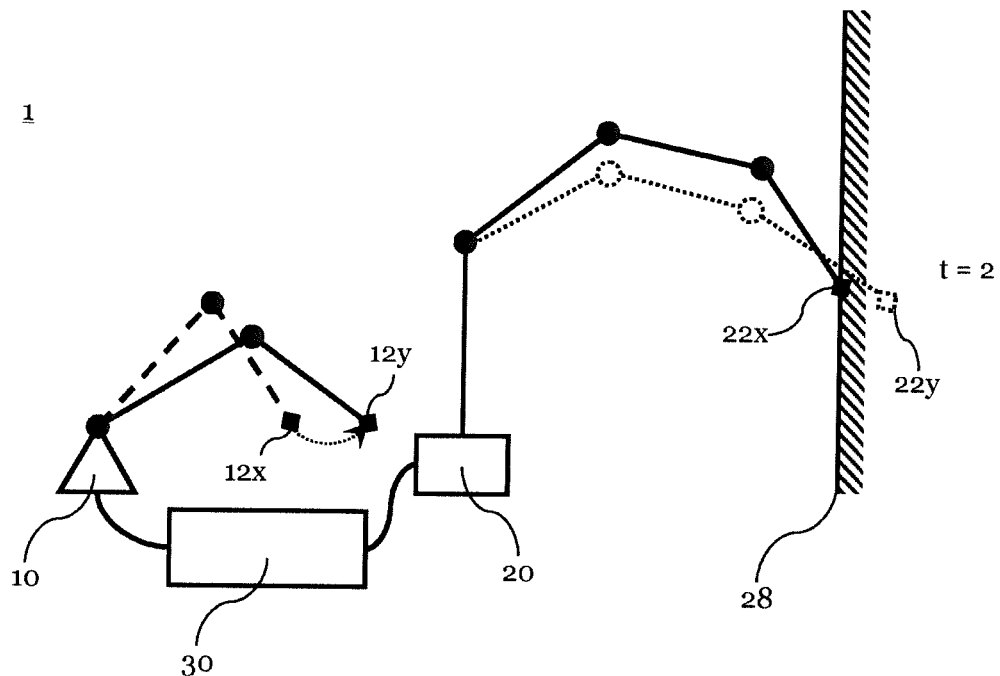
Figure 4C:
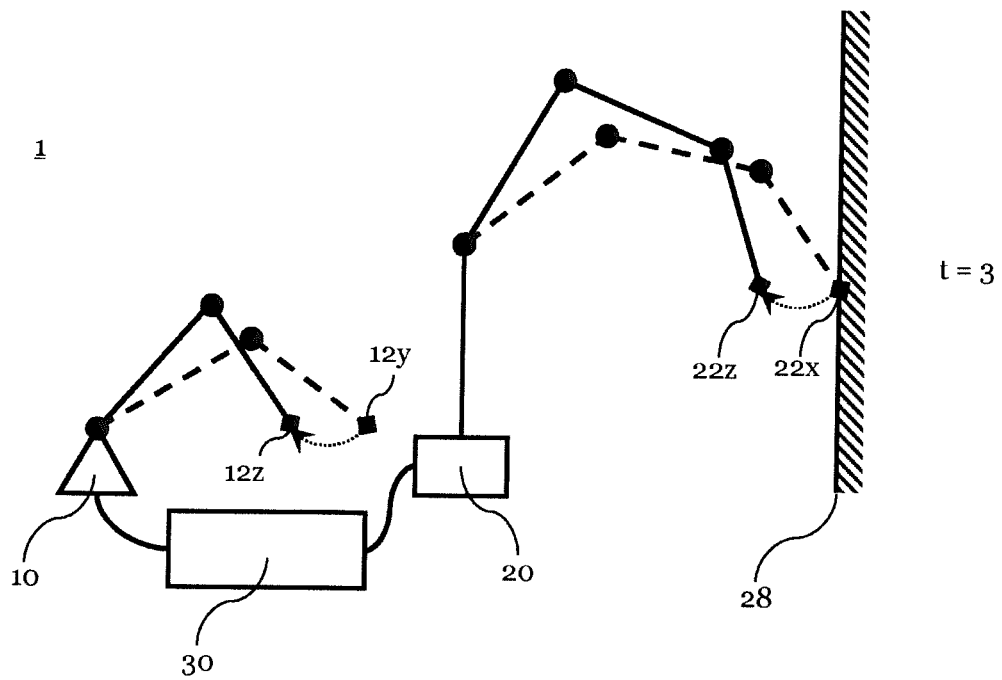

FIGS. 4a to 4c show the manipulator system 1 at the successive times t=1, t=2 and t=3. The corresponding poses of the input point 12 and the reference point 22 are marked with the same letters. For example, the pose 12w of the input point 12 corresponds to the pose 22w of the reference point 22. The individual FIGS. 4a to 4c respectively show a starting position of the input device 10 and the manipulator 20, depicted by the dotted lines, and an end position of the input device 10 and the manipulator 20, depicted by the solid lines. The end position, shown in the preceding figure, corresponds to the starting position, shown in the following figure. Movements are indicated in schematic form by arrows. In addition, the FIGS. 4a to 4c show in schematic form an obstacle space 28, which may not be violated by the reference point 22 of the manipulator 20.

In FIG. 4a the user moves the input point 12 of the input device 10 from the pose 12w to the pose 12x at time t=1 and in this way commands a movement of the reference point 22 from the pose 22w to the pose 22x. This movement is allowed, because the pose 22x of the reference point 22 does not violate the obstacle space 28. The pose 22x is exactly on the border of the obstacle space 28.

In FIG. 4b the user moves the input point 12 of the input device 10 from the pose 12x to the pose 12y at time t=2. The pose 12y corresponds to a pose 22y of the reference point 22, in which the reference point 22 would violate the obstacle space 28. The position of the manipulator 20, which would result in the pose 22y of the reference point 22, is shown by the dotted lines. This potential violation of the obstacle space 28 is detected by the control device 30; and the input device 10 is decoupled from the manipulator 20. Correspondingly the actually commanded movement of the reference point from the pose 22x to the pose 22y is not executed by the manipulator 20. The reference point 22 of the manipulator 20 remains in the pose 22x. Since at this point the input device 10 is decoupled from the manipulator 20, the user can no longer move the manipulator 20 by remote control by manually moving the input device 10.

However, the input device 10 can also be freely operated in the decoupled state. At fixed time intervals the pose of the input point 12 is detected; and initially it is checked whether the commanded pose of the reference point 22 is inside or outside the obstacle space 28. In the case shown in FIG. 4b, the input point 12 was moved into the pose 12y. Since the corresponding pose 22y is, as described above, inside the obstacle space 28 and cannot be approached, the pose 12y of the input point 12 is now mapped to the last allowable pose, in this case the pose 22x of the reference point 22. Consequently, on updating the mapping, the current pose of the input point 12 always corresponds to the last allowable pose of the reference point 22.

In FIG. 4c the user moves the input point 12 of the input device 10 from the pose 12y to the pose 12z at the time t=3. Since the pose 12y is assigned the last allowable pose 22x of the reference point 22, the new commanded pose 22z of the reference point 22 corresponds to a pose, which is outside the obstacle space 28. Consequently at time t=3 the input device 10 can be coupled to the manipulator 20; and the input device 10 can remote control the manipulator 20 with a modified mapping. By continuously updating the mapping of the pose of the input point 12 to the last allowable pose of the reference point 22, the input device 10 can be coupled to the manipulator 20, as soon as the input point 12 is moved in a direction or rotation that faces away from the obstacle space 28. Thus, a faster coupling is possible. Therefore, in this coupling process the mapping of the input device 10 and the manipulator 20 changes continuously in the decoupled state until it is fixed during coupling.

The translational movements, described above, are used merely to simplify the description of the coupling process. However, the manipulator can execute rotational movements and/or combinations of translational and rotational movements just as well, and wherein the preferred method for coupling can be used in the same way.

While the present invention has been illustrated by a description of various embodiments, and while these embodiments have been described in considerable detail, it is not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

List of Reference Numbers and Characters:
1 manipulator system
10 input device
12 input point
12a, b, c, e, w, x, y, z poses of the input point 12
14 input tolerance range
16 extended input tolerance range
20 manipulator
22 reference point
22a, b, c, d, e, w, x, y, z poses of the reference point 22
24 tolerance range of the reference point 22
28 obstacle space
30 control device

What is claimed is:

1. A method for coupling an input device to a robotic manipulator, wherein the input device is configured to control the robotic manipulator, the method comprising:
   a) checking whether the pose of an input point of the input device is within an input tolerance range, wherein the input tolerance range of the input device is determined by mapping a tolerance range of a reference point of the robotic manipulator, and the input tolerance range is unchangeable until the input device is coupled to the robotic manipulator;
   b) allowing limited movement of the reference point of the robotic manipulator to the pose commanded by the input device when the pose of the input point is within the input tolerance range for the purpose of facilitating coupling of the input device to the robotic manipulator; and
   c) coupling the input device to the robotic manipulator after the reference point has reached the commanded pose.

2. The method of claim 1, further comprising:
   d) checking whether the pose of the input point is within an extended input tolerance range and outside the input tolerance range, wherein the extended input tolerance range is greater than the input tolerance range, and wherein the extended input tolerance range comprises the input tolerance range;
   e) determining an approach pose of the reference point, wherein the approach pose is within the tolerance range of the reference point, and the approach pose has a predetermined minimum deviation from the pose of the reference point that is commanded by the input device;
   f) moving the reference point of the robotic manipulator to the approach pose when the pose of the input point is within the extended input tolerance range and outside the input tolerance range; and
   g) coupling the input device to the at least one robotic manipulator after the reference point has reached the approach pose.

3. The method of claim 1, wherein, prior to the step of moving the reference point of the robotic manipulator, the method further comprises:
   h) checking whether the pose of the reference point of the robotic manipulator violates an obstacle space in the input device-commanded pose or the approach pose and, in response to a violation of the obstacle space, stopping movement of the robotic manipulator or guiding the robotic manipulator around the obstacle space.

4. The method of claim 1, comprising:
   terminating movement of the reference point of the robotic manipulator to the input device-commanded pose in step b) when the input point leaves the input tolerance range before reaching the commanded pose; and
   terminating movement of the reference point of the robotic manipulator to the approach pose in step f)

when the input point leaves the extended input tolerance range before reaching the approach pose.

5. The method of claim 1, wherein the shape and/or size of at least one of the tolerance range, the input tolerance range, or the extended input tolerance range is a function of at least one other system variable, wherein the at least one other system variable comprises:
   a) the speed of the manipulator
   b) a detection range that enables the detection of at least one of the position or orientation of the reference point of the robotic manipulator,
   c) forces or torques that act on the reference point of the robotic manipulator,
   d) an obstacle space determined from environmental data, or
   e) a boundary of a working space of the robotic manipulator.

6. The method of claim 2, further comprising:
   automatically determining the extended input tolerance range, wherein the extended input tolerance range corresponds to the input tolerance range scaled by an extension factor.

7. A method for coupling and decoupling an input device to and from a robotic manipulator, wherein the input device is configured to control the robotic manipulator, the method comprising:
   a) decoupling the input device from the manipulator when a reference point of the manipulator has reached an obstacle space or a boundary of a working space;
   b) updating a mapping of the pose of an input point of the input device to the pose of the reference point of the manipulator, wherein a current pose of the input point is mapped to the last allowable pose of the reference point of the manipulator;
   c) checking whether the input device-commanded pose of the reference point of the manipulator in the updated mapping is outside the obstacle space and inside the working space; and
   d) coupling the input device to the manipulator when the input device-commanded pose of the reference point of the manipulator is outside the obstacle space and inside the working space.

8. The method of claim 7, wherein checking whether the input device-commanded pose of the reference point of the manipulator is outside an obstacle space and inside the working space takes place in discrete time steps.

9. The method of claim 7, wherein checking whether the input device-commanded pose of the reference point of the manipulator is outside the obstacle space and inside the working space is a function of a minimum change in the input device-commanded pose of the reference point of the manipulator.

10. The method of claim 1, wherein a speed of the manipulator is a function of at least one system variable, the at least one system variable comprising at least one of:
    a) a detection range that enables the detection of at least one of the position or orientation of the reference point of the manipulator;
    b) forces or torques that act on the reference point of the manipulator;
    c) an obstacle space determined from environmental data; or
    d) a boundary of the working space of the manipulator.

11. The method of claim 1, wherein a change in the pose of the input point of the input device to the change in the pose of the reference point of the manipulator has a translation ratio greater than or equal to 1.

12. The method of claim 1, wherein a change in the pose of the input point of the input device to the change in the pose of the reference point of the manipulator has a translation ratio of 2 to 10.

13. The method of claim 1, wherein a change in the pose of the input point of the input device to the change in the pose of the reference point of the manipulator has a translation ratio of 3 to 5.

14. The method of claim 1, further comprising;
    outputting a haptic, visual, or audible feedback, wherein the feedback indicates at least one of:
        that an obstacle space of the reference point has been reached;
        that the input device has been coupled to or decoupled from the manipulator;
        the distance of the input point of the input device from at least one of the input tolerance range or the extended input tolerance range; or
        that a corresponding allowable pose of the reference point of the manipulator has been reached.

15. The method of claim 1, further comprising:
    graphically displaying the input device-commanded pose of the reference point of the manipulator; and
    virtually superimposing the commanded pose over the actual pose of the reference point of the manipulator.

16. A control device for controlling at least one robotic manipulator with an input device, wherein the control device is configured to receive inputs from the input device and to control the robotic manipulator, the control device including program code stored in a non-transitory, computer-readable storage medium, the program code, when executed on the control device, causing the control device to:
    check whether the pose of an input point of the input device is within an input tolerance range, wherein the input tolerance range of the input device is determined by mapping a tolerance range of a reference point of the robotic manipulator, and the input tolerance range is unchangeable until the input device is coupled to the robotic manipulator;
    move the reference point of the robotic manipulator to the pose commanded by the input device when the pose of the input point is within the input tolerance range; and
    couple the input device to the robotic manipulator after the reference point has reached the commanded pose.

17. A computer program product including program code stored on a non-transitory, computer-readable storage medium, the program code, when executed on a control device for controlling a robotic manipulator, causing the control device to:
    check whether the pose of an input point of an input device is within an input tolerance range, wherein the input tolerance range of the input device is determined by mapping a tolerance range of a reference point of the robotic manipulator, and the input tolerance range is unchangeable until the input device is coupled to the robotic manipulator;
    move the reference point of the robotic manipulator to the pose commanded by the input device when the pose of the input point is within the input tolerance range; and
    couple the input device to the robotic manipulator after the reference point has reached the commanded pose.

* * * * *